US011633354B2

(12) United States Patent
Nikolaidis et al.

(10) Patent No.: US 11,633,354 B2
(45) Date of Patent: *Apr. 25, 2023

(54) CREATINE AND/OR CREATININE COMPOSITIONS AND RELATED METHODS

(71) Applicant: ThermoLife International, LLC, Phoenix, AZ (US)

(72) Inventors: Alexandros Nikolaidis, Nea Kallikratia (GR); Ronald Kramer, Phoenix, AZ (US)

(73) Assignee: THERMOLIFE INTERNATIONAL, LLC, Signal Hill, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/246,473

(22) Filed: Apr. 30, 2021

(65) Prior Publication Data

US 2021/0251895 A1    Aug. 19, 2021

Related U.S. Application Data

(60) Division of application No. 16/541,016, filed on Aug. 14, 2019, now Pat. No. 11,154,499, which is a continuation-in-part of application No. 16/367,209, filed on Mar. 27, 2019.

(60) Provisional application No. 62/650,594, filed on Mar. 30, 2018, provisional application No. 62/648,870, filed on Mar. 27, 2018.

(51) Int. Cl.
| | |
|---|---|
| *A61K 31/4168* | (2006.01) |
| *A61K 47/02* | (2006.01) |
| *A61P 21/06* | (2006.01) |
| *A61K 9/08* | (2006.01) |

(52) U.S. Cl.
CPC ............ *A61K 9/08* (2013.01); *A61K 31/4168* (2013.01); *A61K 47/02* (2013.01); *A61P 21/06* (2018.01)

(58) Field of Classification Search
None
See application file for complete search history.

(56) References Cited

U.S. PATENT DOCUMENTS

| | | | |
|---|---|---|---|
| 5,968,544 A | 10/1999 | Howard | |
| 6,274,161 B1 | 8/2001 | Howard | |
| 6,524,611 B2 | 2/2003 | Howard | |
| 7,150,880 B2 | 12/2006 | Howard | |
| 7,777,074 B2 | 8/2010 | Kramer | |
| 8,354,450 B2 | 1/2013 | Miller | |
| 8,445,466 B2 | 5/2013 | Owoc | |
| 8,952,046 B1* | 2/2015 | Kramer | C07C 275/16 514/400 |
| 9,993,452 B2 | 6/2018 | McDonald | |
| 10,426,750 B1 | 10/2019 | Kramer | |
| 10,435,356 B1* | 10/2019 | Kramer | A23L 2/66 |
| 10,449,157 B2 | 10/2019 | Doherty | |
| 11,154,499 B2* | 10/2021 | Nikolaidis | A61K 9/0019 |
| 11,260,096 B2* | 3/2022 | Kramer | A61K 36/48 |
| 2002/0001611 A1 | 1/2002 | Howard et al. | |
| 2011/0313042 A1* | 12/2011 | Kramer | A61P 21/00 514/565 |
| 2016/0303061 A1 | 10/2016 | Faulkner et al. | |
| 2019/0298667 A1 | 10/2019 | Nikolaidis | |
| 2020/0405799 A1 | 12/2020 | Kramer | |

FOREIGN PATENT DOCUMENTS

| | | |
|---|---|---|
| CN | 104693073 | 6/2015 |
| DE | 10240153 | 3/2004 |

OTHER PUBLICATIONS https://weeklyfitnesstips.com/does-creatinine-help-build-muscle/. Total: 2 pages. Created: Mar. 4, 2016. Accessed: Sep. 13, 2021. (Year: 2016).*

Unal M et al. The effect of acute creatinine monohydrate loading on wingate test results in 18-21 years old male soccer players. Acta Physiologica Hungarica, 2005, 92(3-4), pp. 221-230.

Trexler Eric T. et al. creatine and Caffeine: Considerations for Concurrent Supplementation. International Journal of Sport Nutrition and Exercise Metabolism, 2015, 25(6): pp. 607-623.

Galvan Elfego et al. Acute and chronic safety and efficacy of dose dependent creatine nitrate supplementation and exercise performance. Journal ofthe International Society of Sports Nutrition, 2016, 13:12, pp. 1-24.

National Center for Biotechnology Information. "PubChem Compound Summary for CID 586, Creatine" PubChem, https://pubchem.ncbi.nlm.nih.gov/compound/Creatine. Accessed Aug. 31, 2020. Created Sep. 16, 2004. (Year: 2004).

National Center for Biotechnology Information. "PubChem Compound Summary for CID 588, Creatinine" PubChem, https://pubchem.ncbi.nlm.nih.gov/compound/Creatinine. Accessed Aug. 31, 2020. Created Sep. 16, 2004. (Year: 2004).

Mora et al., "Creatine and creatinine evolution during the processing of dry-cured ham", 2010, Meat Science, 84 (3), pp. 384-389. (Year: 2010).

Lowery et al., "Effects of 8 weeks of Xpand® 2X pre workout supplementation on skeletal muscle hypertrophy, lean body mass, and X strength in resistance trained males", 2013, Journal of the International Society of Sports Nutrition, 10:44, pp. 1-6. (doi: 10.1186/1550-2783-10-44) (Year: 2013).

Joy et al., "28 days of creatine nitrate supplementation is apparently safe in healthy individuals", 2014, Journal of the International Society of Sports Nutrition, 11 :60, pp. 1-6 (doi: 10 1186/s12970-014-0060-9) (Year: 2014).

Ostojic et al., "Searching for a better formulation to enhance muscle bioenergetics: A randomized controlled trial of creatine nitrate V plus creatinine vs. creatine nitrate vs.creatine monohydrate in healthy men", 2019, Food Sci. Nutr., 7 (11 ), pp. 3766-3773. (Year: 2019).

(Continued)

*Primary Examiner* — My-Chau T. Tran (74) *Attorney, Agent, or Firm* — Booth Udall Fuller, PLC; Pacer K. Udall (57) ABSTRACT

The disclosure is directed to methods related to creatinine, for example, a method for its safe administration to a human, a method for using creatinine to improve the bioavailability of creatine, and a metn.

19 Claims, 6 Drawing Sheets

(56) References Cited

OTHER PUBLICATIONS

Craw et al., 1997, "Solvation and solid state effects on the structure and energetics of the tautomers of creatinine", J. Chem. Phys., 106 (16), pp. 6612-6617. (Year: 1997).

Edgar et al., "The Kinetics of the Conversion of Creatine Into Creatinine in Hydrochloric Acid Solutions", 1923, J. Am. Chem. Soc., 45(10), pp. 2242-2245. (doi.org/10.1021/ja01663a003) (Year: 1923).

Griesser, U.J. (2006). The Importance of Solvates. In Polymorphism, R. Hilfiker(Ed.), (https://doi.org/10.1002/3527607889.ch8) (Year: 2006).

* cited by examiner

CREATINE AND/OR CREATININE COMPOSITIONS AND RELATED METHODS

CROSS-REFERENCE TO RELATED APPLICATIONS

This application is a divisional application of U.S. patent application Ser. No. 16/541,016 filed Aug. 14, 2019, which is a continuation-in-part application of U.S. patent application Ser. No. 16/367,209 filed Mar. 27, 2019, which claims priority to and the benefit of U.S. Provisional Patent Application Ser. No. 62/648,870, filed on Mar. 27, 2018, and U.S. Provisional Patent Application Ser. No. 62/650,594, filed on Mar. 30, 2018, the contents of which are hereby incorporated entirely herein by reference.

BACKGROUND

Creatine (Cr) is an endogenous nutrient that occurs in various tissues of mammals, for example, in liver, kidneys, muscular tissue, brain tissue, and blood. It appears in a free state as well as in the form of creatine phosphate. Creatine phosphate (CrP) and creatine are allosteric regulators of cell processes. Creatine enhances the energy tissue metabolism by increasing the energy reserve of ATP in the muscle and nerve cells.

In a cell's mitochondria, creatine interacts reversibly with adenosine triphosphate (ATP) through the action of a creatine kinase enzyme that catalyzes the formation of creatine phosphate and adenosine diphosphate (ADP). Upon consumption of ATP in a cell, a great amount of ADP is released, which leads to a transfer of ortho-phosphate from CrP to ADP, and the initial ratio between ATP and ADP remains. Due to the high affinity of creatine kinase to ADP, this process continues until a creatine phosphate concentration falls below several tens micromolar. This interaction between creatine and ATP maintains the ATP concentration at a constant level at the moments of intense ATP consumption. While other processes exist for replenishing ATP, such as glycolysis or oxidative phosphorylation, these processes refill ATP noticeably slower than the interaction between ATP and creatine.

CrP represents a reserve of macroergic phosphate for maintaining the membrane potential, activation of metabolites or contractive activity of a cell. CrP maintains the ATP level during a period of increasing of energy consumption in a cell, for example, via restoring an ortho-phosphate residue on ADP. Like glycogen, CrP is one of the basic sources of the high-energy phosphates transformation cycle and thereby participates in oxidative phosphorylation of glucose that provides liberation of energy necessary for the functionality of muscular tissue cells, including skeletal muscles and the cardiac muscle. Since CrP provides for regeneration of ATP with a significant speed, an increase of creatine amount in the muscles raises the muscles capacity of CrP, enhances the muscles workability, and increases the muscle bulk.

It has been shown that oral administration of creatine increases the total creatine content in an organism. In particular, administration of creatine monohydrate at dosages up to 30 g for a few days increases the total creatine content in skeletal muscles of a human subject by more than 20%. These properties of creatine make the usage of creatine monohydrate as a dietary supplement or food additive attractive, especially as an addition to the diet of an athlete. As described in the Published International Patent Application WO 94/02127, creatine monohydrate in a daily dose 15 g was administered for at least two days for increasing the muscle force. Nowadays creatine is also recommended as a dietary supplement or food additive for elderly people and vegetarians, as these sections of the population have a tendency to have decreased or low creatine level in their muscles.

Besides the use in the dietary supplement and food industry, creatine and creatine phosphate have wide applications in medicine. For example, creatine and creatine phosphate are recommended for the treatment of nervous system diseases such as diabetic and toxic neuropathies, Alzheimer's disease, Parkinson's disease, and stroke, and also disturbances of metabolism such as hyperglycemia and diabetes mellitus (see U.S. Pat. Nos. 6,706,764 and 6,193,973). Oral administration of creatine has also been disclosed to be useful in the treatment of cardiac insufficiency and respiratory failure (WO/EP97/06225) and of asthma (U.S. Pat. No. 6,093,746). Additionally, creatine phosphate has been disclosed as being useful for the treatment of cardiovascular diseases and for the treatment of new-growth tissue (U.S. Pat. No. 5,219,846).

The modes of delivering creatine has been limited. Ready-to-drink (RTD) formulations and sports drinks, such as Gatorade®, represent a multibillion-dollar market. However, in spite of energy drinks and liquid dietary supplement formulations being very popular among consumers (whether athletes or people seeking to be healthy), there has never been an RTD energy drink, sports drink, or liquid dietary supplement that contains an effective dose of creatine available to consumers. In the past, a "creatine serum" was sold claiming to be the world's first stable liquid creatine preparation. However, test results showed that the product contained less than 2% of the creatine claimed, the rest having been converted to creatinine (Dash and Sawhney, 2002). Creatine salts as well as effervescent forms have been deployed to increase the stability of creatine in aqueous solutions but the results have been disappointing (Ganguly et al, 2003).

The reason for these past failures is because creatine is not stable in aquatic environments, and the rate of degradation increases with decreasing pH. Most drinks have pH of 4.4 or less both to prevent bacterial contamination and for taste purposes. Thus, it is not surprising that to this date no liquid creatine formulation where the creatine can remain stable at room or near room temperature for a prolonged period of time has existed. As such, there is a need for developing compositions and methods that offer the benefits of a stable liquid creatine product.

SUMMARY

The disclosure relates to compositions and methods that ensure the stability of creatine. The disclosure also relates to compositions of creatine and creatinine where the creatinine enhances the concentration of creatine, bioavailability of creatine, maximum plasma concentration ($C_{max}$) of creatine, or total plasma concentration of creatine over time (in human subjects), for example, as evidenced by area under the curve (AUC) of creatine in subjects. In some embodiments, the composition is a solid composition comprising a creatine compound such as creatine nitrate and creatinine or a suitable creatinine compound. In some aspects, the compositions described herein are dietary supplements or dietary supplement formulations, for example, a nutraceutical drink product, a liquid food product, or a fortified food for example.

In some aspects, the ratio of the creatine compound to creatinine or a suitable creatinine compound by weight in the composition is between 23:1 and 1:9. In some aspects, the molar ratio of the creatine compound to creatinine or a suitable creatinine compound in the composition is between 20:1 and 1:9, between 2:1 and 1:4, or between 3:1 and 1:3. In a certain embodiment, the molar ratio of the creatine compound to creatinine or a suitable creatinine compound in the composition is 1:1.7. In a certain embodiment, the composition comprises 5 g of creatine nitrate and 5 g of creatinine. In another embodiment, the composition comprises 3 g creatine nitrate and 3 g creatinine in about 475 ml or 16 oz of liquid in a ready-to-drink sports supplement formulation. In still another embodiment, the composition comprises 1.5 g creatine nitrate, 3.5 g creatine monohydrate, and 5 g creatinine. In other aspects, the weight of the creatinine compound is 5% to 800% the weight of the creatine compound, for example, the weight of the creatinine compound is between 50% and 200% of the weight of the creatine compound. In another embodiment, the composition is in a liquid form made from mixing the solid composition with water or a water-based composition. Thus, the liquid composition comprises a creatine compound (preferably creatine nitrate, for example), creatinine or a suitable creatinine compound, and water. For example, the composition comprising 1.5 g creatine nitrate, 3.5 g creatine monohydrate, and 5 g creatinine is dissolved in water or a water-based composition. In a preferred embodiment, the resulting liquid composition has a pH of 4.4 or less, for example between 4.2 and 4.4 or about 4.4. In some aspects, the total volume of the liquid composition is about 16 fluid ounces or about 450 ml.

In some embodiments, the composition, whether liquid or solid, comprises one or more additional components selected from the group consisting of a carrier, an excipient, a binder, a colorant, a flavoring agent, a preservative, a buffer, and a diluent. In some aspects, the compositions of the invention may be in a dosage form selected from the group consisting of: a capsule, a cachet, a pill, a tablet, an effervescent tablet, a powder, a granule, a pellet, a bead, a particle, a troche, a lozenge, a gel, a liquid, a suspension, a solution, an elixir, and a syrup.

The compositions disclosed herein may be used as a food additive, nutraceutical, or dietary supplement, such as, for example, an addition to the diet of a healthy person, a patient, an athlete, and the like. These compositions may also be used in preparation of liquid formulations intended for use by patients where creatine supplementation would be beneficial, such as with patients suffering from cerebral creatine deficiency syndromes, chronic obstructive pulmonary disease (COPD), congestive heart failure (CHF), depression, diabetes, fibromyalgia, Huntington's disease, idiopathic inflammatory myopathies (polymyositis, dermatomyositis), Parkinson's disease, mitochondrial myopathies, multiple sclerosis, muscle atrophy, muscle cramps, neonatal apnea, neurological trauma, Rett syndrome, gyrate atrophy of the choroid and retina, hereditary motor and sensory neuropathy, schizophrenia, spinal muscular atrophy, and surgical recovery, amyotrophic lateral sclerosis (ALS, also known as Lou Gehrig's disease), osteoarthritis, rheumatoid arthritis, McArdle disease, and various muscular dystrophies. Additionally, such compositions may also be used in either oral or parenteral nutrition. Furthermore, the compositions could also be used topically in liquid or semiliquid formulations such as creams, emulsions, serums, solutions, spirits, aerosols, gels and the like to promote skin health and prevent skin aging.

The disclosure is also directed to a method of stabilizing creatine in a liquid wherein the creatine content of the liquid composition after a month of storage at room or near room temperature is at least 70% of the amount of creatine originally placed in the liquid. In other aspects at least 90% or 95% of the original creatine placed in the liquid remains after storage of a month or 3 months or 6 months or a year. Stability of at least 90% of the original amount of creatine is critical, because US Pharmacopoeia formulation guidelines require that ingredients, such as creatine, must have at least 90% of the amount stated in the label. The method may include: providing an amount of creatine; providing an amount of creatinine; dissolving the amount of creatine in water to produce a liquid composition; and adding the amount of creatinine to the liquid composition. The amount of creatine is provided from an acceptable form of creatine, including, an anhydrous form, a salt, a solvate, or a hydrate (for example, anhydrous creatine, creatine monohydrate, creatine formic acid solvate, or preferably creatine nitrate). The amount of creatinine is provided from an acceptable form of creatinine, including, an anhydrous form, a salt, a solvate, or a hydrate.

In certain implementations of the method, the amount of creatine and the amount of creatinine are combined in water to produce the liquid composition. Thus, in some aspects, the steps of dissolving the amount of creatine in water to produce a liquid composition and adding the amount of creatinine to the liquid composition consist of dissolving the amount of creatine and the amount of creatinine in water. Where the amount of creatine and the amount of creatinine are combined with water at different times, the amount of creatinine is added to the liquid composition formed from dissolving the amount of creatine in water no more than a day after the amount of creatine is dissolved in water. Accordingly, in some aspects, the amount of creatinine is dissolved first, and there is no time limit for when the amount of creatine is added to the liquid composition.

In some implementations of the methods, the weight of the amount of creatinine or salt or hydrate thereof is 5% to 800% the weight of the amount of creatine, for example, the weight of the amount of creatinine or salt or hydrate thereof is between 50% and 200%. In other implementations, the molar ratio of the amount of creatine to the amount creatinine or salt or hydrate thereof is between 2:1 and 1:4 or between 3:1 and 1:3, for example, in the case of creatine nitrate and creatinine about, 1:1.7. In certain implementations, the amount of creatine nitrate is 5 g and the amount of creatinine is 5 g.

The disclosure also relates to methods of improving the solubility of creatine in water and to methods of producing a composition for parenteral administration or intravenous administration of creatine to humans. In certain embodiments, the methods are directed to increasing the creatine-stabilizing effect of creatinine in an aqueous solution comprising creatine. These methods comprise providing an aqueous solution comprising an amount of creatine and an amount of creatinine and adding an amount of nitrate ($NO_3^-$) to the aqueous solution comprising creatine. In certain embodiments, the methods are directed to enhancing conversion of creatinine to creatine in an aqueous solution. These methods comprise providing an aqueous solution comprising an amount of creatinine and adding to the aqueous solution an amount of nitrate ($NO_3^-$). In some implementations of these methods, the aqueous solution further comprises an amount of creatine. The amount of creatine in the aqueous solution (or water) remains stable at a wide range of storage temperature, for example, between refrigeration and room temperature.

In some aspects of the methods of increasing the creatine-stabilizing effect of creatinine in an aqueous solution comprising creatine and of the methods of enhancing conversion of creatinine to creatine in an aqueous solution, the molar ratio of the amount of nitrate ($NO_3^-$) to the amount of creatinine is selected from the group consisting of: between about 20:1 and about 1:9, between about 10:1 and about 1:1, between about 3:1 and about 1:3, and between about 2:1 and about 1:4. In some implementations, molar ratio of the amount of creatine to the amount of nitrate ($NO_3^-$) is selected from the group consisting of: between about 20:1 and about 1:9, between about 10:1 and about 1:1, between about 3:1 and about 1:3, and between about 2:1 and about 1:4. In certain implementations, the molar ratio of the amount of creatine to the amount of nitrate ($NO_3^-$) is 1:1.

Methods of increasing the bioavailability of creatine and to counter the negative effect of caffeine on creatine supplementation are also disclosed. In one aspect, the method of improving the bioavailability of creatine comprises co-administering to a human subject desiring the benefits of creatine supplementation with an effective amount of creatine, creatinine, and nitrate ($NO_3^-$). Methods of safely administering creatinine to a subject in need thereof, for example for five days or longer, are also disclosed.

In some aspects of the method of increasing the bioavailability of creatine and of the method of safely administering creatinine to a subject in need thereof, the effective amount of creatine administered is at least 500 mg, the effective amount of creatinine administered is at least 500 mg, and the effective amount of nitrate ($NO_3^-$) administered is at least 50 mg nitrate ($NO_3^-$). In other implementations, the effective amount of creatine administered is at least 1000 mg, the effective amount of creatinine administered is at least 1000 mg, and the effective amount of nitrate ($NO_3^-$) administered is at least 100 mg nitrate ($NO_3^-$). In still other implementations, the effective amount of creatine administered is at least 2 g, the effective amount of creatinine administered is at least 2 g, and the effective amount of nitrate ($NO_3^-$) administered is at least 250 mg. In yet another implementation, the effective amount of creatine administered is at least 2 g, the effective amount of creatinine administered is at least 2 g, and the effective amount of nitrate ($NO_3^-$) administered is at least 500 mg. In another implementation, the effective amount of creatine administered is at least 5 g, the effective amount of creatinine administered is at least 3 g, and the effective amount of nitrate ($NO_3^-$) administered is at least 1000 mg.

DETAILED DESCRIPTION

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that implementations of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "about" refers to a deviation up to but not more than 10% of the given value, for example a deviation of 10%, 7.5%, 5%, 4%, 3%, 2%, 1%, 0.5%, or 0.1% of the given value.

As used herein, the term "dietary supplement" refers to an addition to the human diet which is not a natural food, which has additional beneficial effects on the body unattainable by regular nutrition. In some aspects, a dietary supplement is manufactured to be used over time, allowing for precise dosing. In some aspects, a dietary supplement includes fortified food.

As used herein, the term "nutraceutical" refers to a dietary supplement, a dietary ingredient, a food additive, or a fortified food that provides health benefits, including preventing, treating, or curing a physical or mental condition.

As used herein, the term "dietary ingredient" refers to a dietary substance for use by man to supplement the diet by increasing total dietary intake.

As used herein, the term "food additive" refers to a substance that is a component added to food.

As used herein, the term "fortified food" refers to food where its nutritional and health value is increased (or fortified) by the additional of a dietary supplement, dietary ingredients, or food additive.

As used herein, the term "room temperature" encompasses of a range of temperatures between about 15° C. and about 27° C., for example, between about 15° C. and about 25° C., between about 18° C. and about 22° C., or about 20° C.

As used herein, the time period of "a day" refers to a period of between 18 and 30 hours, for example, between 22 and 26 hours or about 24 hours.

As used herein, the term "effective amount" refers to an amount that induces a measurable or observable physiological change in a human. For example, in certain embodiments, an effective amount of creatinine refers to an amount of creatinine that increases the bioavailability of creatine or an amount that counteracts the inhibitory effect of caffeine on the ergogenic effects of creatine.

The present disclosure addresses the need for ensuring the stability of creatine in a solution, for example of water or other liquid or water-based formulations.

Whereas solid creatine is stable, the presence of water leads to intramolecular cyclization that converts creatine to creatinine (see Scheme 1).

Scheme 1

The rate of creatine degradation in solution is not dependent on the concentration of creatine but on the pH of the solution. Generally, the lower the pH and higher the temperature, the faster creatine becomes creatinine in solution (see, for example, Edgar and Shiver, 1925; Cannon et al., 1990; Dash et al., 2002). While creatine was relatively stable in solution at neutral pH (7.5 or 6.5), lowering of pH resulted in an increased rate of degradation. After only three days of storage at 25° C., creatine degraded by 4% at pH 5.5, by 12% at pH 4.5, and by 21% at pH 3.5. Similarly, creatine monohydrate in solution stored at room temperature degraded into creatinine within several days, while refrigerating creatine monohydrate in solution slowed the rate of degradation (Ganguly et al., 2003). Accordingly, the rapid degradation of creatine in solution precludes the manufacture of shelf-stable beverages containing efficacious amounts of the ingredient.

Another issue with creatine supplementation has been its limited bioavailability and finding methods to improve its bioavailability as well as its overall plasma levels. In the past it was erroneously assumed that creatine possesses a bioavailability of near 100% because of a 2007 article that assumed that since no creatine or creatinine was detected in feces, the bioavailability of creatine should be around 100% (Deldicque et al., 2008). However recent data from a radiokinetic bioavailability study (a standard for pharmacokinetic studies that produces more detailed and accurate data than merely measuring the contents of an orally administered compound excreted) indicated that this hypothesis is highly erroneous; in fact, creatine bioavailability was shown to be sharply reduced with increasing doses (Alraddadi et al., 2018). This finding validated the hypothesis by McCall and Persky that creatine bioavailability is less than 100% because of bacterial flora degradation in the gastrointestinal tract, gastric degradation, site dependent intestinal absorption and incomplete dissolution of creatine solid dosage forms (McCall and Persky, 2007).

It was surprisingly discovered by the inventors that the presence of creatinine in a solution comprising creatine reduces the rate of creatine degradation, and in some cases, creatine degradation is eliminated. Therefore, the present disclosure is directed in part to a liquid composition (for example, a liquid food product or liquid dietary supplement formulation) containing a creatine compound and a creatinine compound wherein the creatine is stable for at least one month when stored at room temperature or near room temperature. The liquid also possesses increased stability, for example of creatine, during refrigerated storage.

The disclosure also relates to methods of stabilizing creatine in a liquid wherein the creatine content of the liquid composition after a month, two months, or three or more months or over a year of storage at about room temperature or no greater than room temperature is at least 70% of the amount of creatine nitrate provided thus enabling the preparation of a liquid dietary supplement formulation comprising stable creatine. In some aspects, the methods of stabilizing creatine in a liquid results the amount of creatine in the liquid composition being at least 90% or at least 95% of the amount of creatine nitrate provided after a month, two months, or three or more months or over a year of storage at about room temperature or no greater than room temperature. The methods comprise providing an amount of creatine (for example, provided as a creatine compound selected from the group consisting of anhydrous creatine and a salt or hydrate or solvate of creatine); providing an amount of creatinine (for example, provided as a creatinine compound selected from the group consisting of anhydrous creatinine and a salt or hydrate or solvate of creatinine); and dissolving the amount of creatine and/or the amount of creatinine in water or a water-based composition. In some aspects, the water-based composition is a ready-to-drink food product, dietary supplement, vegetable juice, or fruit juice.

In some implementations, the amount of creatine is first dissolved in water or water-based composition to produce a liquid composition and the amount of creatinine is then added to the liquid composition. In a preferred implementation, the amount of creatinine is added to the liquid composition, preferably no more than a day after creatine is dissolved in water or water-based composition. However, creatinine may be added to the liquid composition formed from dissolving creatine in a liquid more than a day after the creatine is dissolved. In such implementations, precise formulation and labeling for the resulting composition is difficult as creatine may have degraded a significant amount according to labeling regulations.

In other implementations, the amount of creatine and the amount of creatinine are both dissolved in water or water-based composition to produce a liquid composition, which can also be the liquid food product or liquid dietary supplement formulation.

In still other implementations, the amount of creatinine is first dissolved in water or water-based composition to produce a liquid composition, and the amount of creatine is then dissolved in the liquid composition at a later time. In such implementations, the timing of when creatine is dissolved in the liquid composition is not important, as the dissolved creatinine does not lose its ability to stabilize creatine in water over time.

In some implementations of the methods, the weight of the amount of creatinine or salt or hydrate thereof is 5%-800% or 50-200% the weight of the amount of creatine compound. In other implementations, the molar ratio of the amount of the creatine compound to the amount of the creatinine or salt or hydrate thereof is between about 23:1 and 1:9, for example, between 20:1 and 1:9, between 2:1 and 1:3, between 3:1 and 1:3, 1:1, or 1:1.7. In some embodiments, the creatine compound provides at least 500 mg creatine, at least 1000 mg creatine, at least 2 g creatine, or at least 5 g creatine, while the amount of creatinine provided is at least 500 mg, at least 1000 mg, at least 2 g, or at least 3 g. In certain implementations, the amount of creatine nitrate is 5 g and the amount of anhydrous creatinine is 4 g. In another implementation, the amount of the creatine compound consists of 1.5 g creatine nitrate and 3.5 g anhydrous creatine while the amount of creatinine compound consists of 5 g anhydrous creatinine. In another implementation, the amount of the creatine compound consists of 3 g creatine nitrate and 2 g anhydrous creatine while the amount of creatinine compound consists of 5 g creatinine.

In some implementations of the methods for increasing the stability of creatine in solution, the methods further comprise providing at least one source of nitrate ($NO_3^-$), wherein the at least one source of nitrate ($NO_3^-$) is dissolved with the creatine compound and/or the creatinine compound in water or water-based composition. In such implementations, the source of nitrate ($NO_3^-$) enhances the conversion of creatinine to creatine in the solution. Thus, such methods increase the creatine-stabilizing effect of creatinine in an aqueous solution and enhances conversion of creatinine to creatine in an aqueous solution. Accordingly, in some aspects, the disclosure is also directed to methods of increasing the creatine-stabilizing effect of creatinine in an aqueous solution and to methods of enhancing the conversion of creatinine to creatine in an aqueous solution.

In some implementations, the amount of nitrate ($NO_3^-$) provided by the at least one source of nitrate ($NO_3^-$) results in a molar ratio with the amount of creatinine of between about 20:1 and about 1:9, between about 10:1 and about 1:1, between about 3:1 and about 1:3, or between about 2:1 and about 1:4. In some implementations, the amount of nitrate ($NO_3^-$) provided by the at least one source of nitrate ($NO_3^-$) results in a molar ratio with the amount of creatine of between about 20:1 and about 1:9, between about 10:1 and about 1:1, between about 3:1 and about 1:3, or between about 2:1 and about 1:4. In certain embodiments, the molar ratio of the amount of creatine to the amount of nitrate ($NO_3^-$) provided by the at least one source of nitrate ($NO_3^-$) is 1:1. In such embodiments, the source of nitrate ($NO_3^-$) may be creatine nitrate. In some aspects, the at least one source of nitrate ($NO_3^-$) provides at least 50 mg nitrate ($NO_3^-$), at least 100 mg nitrate ($NO_3^-$), at least 250 mg nitrate ($NO_3^-$), at least 500 mg nitrate ($NO_3^-$), at least 100 mg nitrate ($NO_3^-$), between 50 mg and 1200 mg nitrate ($NO_3^-$), between 60 mg and 1200 mg nitrate ($NO_3^-$), between 50 mg and 1500 mg nitrate ($NO_3^-$), or between 60 mg and 1500 mg nitrate ($NO_3^-$).

In some embodiments, the method further comprises adjusting the pH of the liquid composition (after the creatine compound and the creatinine compound are dissolved) to 4.4 or less, for example, between about 4.2 and about 4.4. The pH can be adjusted using any acceptable pH buffer, for example, sodium hydroxide.

In some aspects, the disclosure also relates to a liquid composition comprising creatine and creatinine, for example a drink fortified with creatine and creatinine, wherein the liquid composition comprises a stable amount of creatine. The stable liquid creatine formulation is produced by combining a creatine compound and creatinine compound into a composition and then dissolving the composition in water or a water-based composition. In other implementations, either the creatine compound or the creatinine compound is dissolved in water or water-based composition before the other compound is dissolved. The order of which of the creatine compound or the creatinine compound is dissolved first in water or the water-based composition is not critical, though dissolved creatine should not be allowed to remain in water or water-based composition alone for more than an hour. For example, creatine monohydrate can first be dissolved in 500 ml of water, and an hour later, creatinine is dissolved in the same solution. If the creatinine compound is dissolved in water or water-based composition first, there is no similar urgency for when the creatine compound is dissolved in the resulting solution. In some preferred implementations, the creatinine compound is first dissolved in water or water-based composition. In some implementations, the liquid composition is produced by first mixing the creatine compound and the creatinine compound separately in water to produce two separate solutions and then mixing the two solutions.

In some embodiments, the stable liquid creatine formulation further comprises reducing the water content of the composition or thickening the composition. Accordingly, in some aspects, the stable liquid creatine formulation is semisolid, for example, in the form of an emulsion, a pudding, or a gel.

In another implementation, the creatine compound and the creatinine compound are dissolved in water or water-based composition separately to produce a creatine solution and a creatinine solution before the two solutions are combined to produce a liquid composition described herein. To ensure no significant degradation of creatine takes place (for example, more than 90% of the creatine provided is degraded), the two solutions are combined within a day, or preferably within one hour dissolving the creatine compound. In some aspects, the method further comprises thickening or reducing the moisture content of the creatine solution and/or the creatinine solution, wherein combining the two solutions produces a semisolid composition or semiliquid composition, for example, a gel or pudding. In other aspects, the method further comprises thickening or reducing the liquid composition to produce a semisolid composition, for example, a gel or pudding.

In some embodiments, the stable liquid creatine formulation has a pH of 4.4 or less, for example, between 4.2 and 4.4 or preferably about 4.4. Accordingly, in some implementations, the method of producing the stable liquid creatine formulation further comprises buffering the solution containing the dissolved creatine compound and the dissolved creatinine compound to a pH of 4.4 or less, for example, between 4.2 and 4.4 or about 4.4.

In some aspects, the invention is also directed to solid compositions comprising a creatine compound and creatinine compound. In some aspects, the weight of the creatinine compound is 5%-800% or 50-200% the weight of the creatine compound. In a preferred embodiment, the weight of the creatinine provided by the creatinine compound is 5%-800% or 50% to 200% the weight of creatine provided by the creatine compound. In other implementations, the molar ratio of the creatine compound to the creatinine compound is between about 23:1 and 1:9, for example, between 20:1 and 1:9, between 2:1 and 1:3, between 3:1 and 1:3, 1:1, or 1:1.7. In some embodiments, the creatine compound provides at least 500 mg creatine, at least 1000 mg creatine, at least 2 g creatine, or at least 5 g creatine, while the amount of creatinine provided is at least 500 mg, at least 1000 mg, at least 2 g, or at least 3 g. In one embodiment, the creatine compound in the composition is 5 g creatine nitrate and the creatinine compound is 4 g anhydrous creatinine. In another embodiment, the amount of the creatine compound in the composition consists of 1.5 g creatine nitrate and 3.5 g anhydrous creatine, while the amount of creatinine compound in the composition consists of 5 g anhydrous creatinine. In still another embodiment, the amount of the creatine compound in the composition consists of 3 g creatine nitrate and 2 g anhydrous creatine, while the amount of creatinine compound in the composition consists of 5 g creatinine.

In certain embodiments, the compositions including creatine and creatinine are dietary supplements, for example, to increase the amount of creatine in one's diet. As such, in some aspects, the disclosure is also directed to the use of creatinine as a dietary ingredient or as a food additive.

Prior to the present disclosure, creatinine was primarily considered a waste product from the normal breakdown of muscle tissue. As creatinine is produced, it is filtered through the kidneys and excreted in urine. To this day, no beneficial biological role for creatinine has been established. In contrast, creatinine is believed to be a toxic compound which can impair human performance and health. Tambaru et al. and Gangopadhya et al. both describe creatinine as a compound which can cause kidney damage. In view of high levels of creatinine being correlated with a bad health prognosis, such as high creatinine levels in the urine indicating kidney failure, it would be unethical to study the biological effects caused by extremely high levels of creatinine in humans. While it would be unethical to administer extremely high levels of creatinine in a human subject, animal studies have supported the avoidance of supplementing creatinine or taking action that results in high creatinine levels in the blood, tissues, or urine. In mice, administration of creatinine had a sedating or stupefying effect from an injection of creatinine (see Lis and Bijan, 1970). A similar effect was seen in dogs (Giovannetti et al., 1969). In addition to their observations of the animal's aberrant behavior, Giovannetti et al. further concluded that creatinine was also responsible for a significant decrease in the animal's erythrocyte survival time. In human blood cells, the addition of creatinine initiated a significant increase in spontaneous hemolysis. This same red cell lysing pattern was observed in normal human volunteers whom had ingested creatinine (Giovannetti et al., 1969). Barsotti's research in 1975 gave further evidence of this potential membrane-associated molecular blockade by showing that creatinine was able to effectively inhibit glucose utilization by erythrocytes (Barsotti et al., 1975).

Often creatinine is found in creatine supplements, but due to the evidence suggesting extra creatinine would have deleterious effects, creatinine is considered an impurity in such compositions. Accordingly, strict regulations exist to limit the amount of creatinine in commercial creatine powders, for example, Health Canada allows the import of creatine monohydrate powders that contain a maximum of 100 ppm creatinine (0.01% or less by weight).

It was also surprisingly discovered that, in contrast to prior art describing creatinine as toxic, a waste product, useless, and harmful to human performance (athletic, mental, and otherwise), concomitant administration of creatine and creatinine to human subjects actually yield beneficial effects. As shown in Example 7, concomitant administration of creatine and creatinine resulted in improved creatine bioavailability, improved creatine maximum concentration, and improved creatine body utilization. Instead of hindering performance, creatinine actually increased the ergogenic effects of creatine without producing any toxic or performance inhibiting effects.

In some aspects, the disclosure relates to methods of increasing the bioavailability of creatine, the method comprising administering a creatine compound in combination with a creatinine compound. The method also results in greater serum concentration of creatine, greater muscle utilization of creatine, or overall beneficial effect of creatine. As demonstrated in Example 7, no negative effects are associated with co-administration of a creatine compound with a creatinine compound. Accordingly, the disclosure also relates to methods of safely administering creatinine to a subject in need thereof. In some implementations, an amount of between 0.5 and 20 g creatine is administered by the administration of the creatine compound and an amount of between 0.5 and 20 g creatinine is administered by the administration of the creatinine compound. For example, at least 1.5 g creatine, for example at least 2 g creatine is administered through the administration of the creatine compound. In some implementations, at least 1.5 g creatinine is administered through the administration of the creatinine compound, for example when the amount of creatine administered is at least 2 g.

In some aspects, the method of increasing the bioavailability of creatine further comprises administering an effective amount of a source of nitrate ($NO_3^-$). Such methods also safely administered creatinine to a subject in need thereof. In some embodiments, the creatine compound provides at least 500 mg creatine, at least 1000 mg creatine, at least 2 g creatine, or at least 5 g creatine; the amount of creatinine provided is at least 500 mg, at least 1000 mg, at least 2 g, or at least 3 g; and the amount of nitrate ($NO_3^-$) provided by the source of nitrate ($NO_3^-$) is at least 50 mg, at least 100 mg, at least 250 mg, at least 500 mg, or at least 1000 mg. In certain embodiments, the amount of nitrate ($NO_3^-$) provided by the source of nitrate ($NO_3^-$) is between between 50 mg and 1200 mg nitrate ($NO_3^-$), between 60 mg and 1200 mg nitrate ($NO_3^-$), between 50 mg and 1500 mg nitrate ($NO_3^-$), or between 60 mg and 1500 mg nitrate ($NO_3^-$).

As demonstrated in Example 9, Applicants also surprisingly discovered that solubility of creatine in water at standard temperature and ambient pressure can be increased without the need to reduce the pH of the solution with the presence of creatinine. Accordingly, this disclosure also relates to a method of increasing the solubility of creatine in water. The method comprises adding a creatine compound to a water-based composition comprising creatinine to create a creatine solution. A benefit of this method is that the resulting composition comprising dissolved creatine can have a pH of between about 7 and about 8, which makes the composition suitable for parenteral administration, such as intravenous administration. In some aspect, the water-based composition comprising creatinine is produced by dissolving a creatinine compound in water or a water-based composition. In some implementations, the method further comprises adjusting the pH of the creatine solution to a pH of between about 7 and about 8. In some aspects, methods are also directed to method of producing a composition for parenteral or intravenous administration of creatine to humans. In one implementation, the weight of the creatine in the water-based composition is 50 to 500% the weight of the creatine provided by the creatine compound.

It was also surprisingly discovered that co-administration of a creatinine compound with a creatine compound counteracted caffeine's neutralizing effect on the ergogenic actions of creatine (see Example 8). Thus, in some aspects, this disclosure also relates to a method of neutralizing caffeine's negative effect on the ergogenic actions of creatine, where the method includes administering to a subject consuming caffeine an effective amount of creatinine or a combination of an effective amount of a creatine compound and an effective amount of a creatinine compound. For a subject consuming between 60 to 1200 mg caffeine per day, the effective amount of creatine and creatinine administered to ensure the effectiveness of dietary supplementation of creatine is between 1-30 g creatine per day and between 1-30 g creatinine per day, for example, about 20 g creatine and about 20 g creatinine per day. In certain implementations, the daily amount of creatine and creatinine is administered in multiple doses in a day, for example split across two, three, or four doses.

In some aspects, the creatinine compound and/or the creatine compound is/are administered to the subject consuming caffeine within a day of the consumption of caffeine. In some implementations, the creatine compound and the creatinine compound are administered separately. For example, the creatinine compound is administered to the subject within a day, about 24 hours, or about 2 hours of the administration of the creatine compound. In other implementations, the creatine compound and the creatinine compound are administered in a dietary supplement composition comprising an effective amount of the creatine compound and an effective amount of the creatinine compound.

Thus, Applicants discovered that creatinine is suitable as a dietary ingredient or food additive. In view of creatinine's beneficial supportive role in creatine supplementation, the disclosure also relates to the use of creatinine in producing a food fortified with creatine. As such, the disclosure also relates to dietary supplements and fortified foods comprising creatine.

In some implementations of the methods for neutralizing caffeine's prohibitive effect on the ergogenic actions of creatine, the methods further comprises administering to the subject consuming caffeine at least one source of nitrate ($NO_3^-$). In some aspects, the at least one source of nitrate ($NO_3^-$) provides at least 50 mg, at least 100 mg, at least 250 mg, at least 500 mg, or at least 1000 mg. In certain embodiments, the amount of nitrate (NO) provided by the source of nitrate ($NO_3^-$) is between 50 mg and 1200 mg nitrate ($NO_3^-$), between 60 mg and 1200 mg nitrate ($NO_3^-$), between 50 mg and 1500 mg nitrate ($NO_3^-$), or between 60 mg and 1500 mg nitrate ($NO_3^-$).

In some implementations of using creatinine as a dietary ingredient or food product, the dietary supplement or food product comprises at least one source of nitrate ($NO_3^-$). In some aspects, the at least one source of nitrate ($NO_3^-$) provides at least 50 mg, at least 100 mg, at least 250 mg, at least 500 mg, or at least 1000 mg. In certain embodiments, the amount of nitrate ($NO_3^-$) provided by the source of nitrate ($NO_3^-$) is between 50 mg and 1200 mg nitrate ($NO_3^-$), between 60 mg and 1200 mg nitrate ($NO_3^-$), between 50 mg and 1500 mg nitrate ($NO_3^-$), or between 60 mg and 1500 mg nitrate ($NO_3^-$).

In some implementations of methods of producing a food fortified with creatine, the methods further comprise adding to the food fortified with creatine at least one source of nitrate ($NO_3^-$). In other aspects, the food fortified with creatine comprises at least one source of nitrate ($NO_3^-$). In some aspects, the at least one source of nitrate ($NO_3^-$) provides at least 50 mg, at least 100 mg, at least 250 mg at least 500 mg, or at least 1000 mg. In certain embodiments, the amount of nitrate ($NO_3^-$) provided by the source of nitrate ($NO_3^-$) is between 50 mg and 1200 mg nitrate ($NO_3^-$), between 60 mg and 1200 mg nitrate ($NO_3^-$), between 50 mg and 1500 mg nitrate ($NO_3^-$), or between 60 mg and 1500 mg nitrate ($NO_3^-$).

In some implementations of the methods of increasing the solubility of creatine in water, the methods further comprise adding at least one source of nitrate ($NO_3^-$) to the water-based composition comprising creatinine. In some aspects, the at least one source of nitrate ($NO_3^-$) provides at least 50 mg, at least 100 mg, at least 250 mg, at least 500 mg, or at least 1000 mg. In certain embodiments, the amount of nitrate ($NO_3^-$) provided by the source of nitrate ($NO_3^-$) is between 50 mg and 1200 mg nitrate ($NO_3^-$), between 60 mg and 1200 mg nitrate ($NO_3^-$), between 50 mg and 1500 mg nitrate ($NO_3^-$), or between 60 mg and 1500 mg nitrate ($NO_3^-$).

The amount of creatine compound in the compositions of the invention (for both the solid composition and the liquid composition) is variable depending on the desired supplemental amount of creatine. Generally, a dose of creatine for supplementation includes amounts between 500 mg to 25 g creatine per dose. However, the molar ratio of the creatine compound and creatinine compound in the compositions of the invention may be between about 23:1 and about 1:9, for example, between about 20:1 and about 1:3, between about 10:1 and about 1:1, between about 3:1 and about 1:3, between about 2:1 and about 1:1, about 1:1 or about 1:1.7. In some aspects, the amount of creatinine compound is between 5% and 800% (for example between 50% and 200%) the weight of creatine compound. In certain embodiments, for example, where the dietary ingredients of the dietary supplement consist of a creatine compound and a creatinine compound, the ratio by weight of creatine (from the creatine compound) to creatinine (from the creatinine compound) is preferably 5.5-7 weight parts creatine to 8 weight parts creatinine. It is preferred that only minimal amount of the creatinine compound (lowest amount possible to produce the desired effect, such as increased solubility or bioavailability of creatine or increased stability of creatine in solution) is included in the compositions of the invention. For example, in certain embodiments, the molar ratio of the creatine compound to the creatinine compound is about 1:1.1 or about 1:1.7.

One exemplifying composition comprises about 5 g creatine nitrate (which corresponds to the composition providing about 3.34 g creatine) and about 4 g creatinine. Another exemplifying composition comprises about 5 g creatine nitrate and about 5 g anhydrous creatinine. Still another exemplifying composition comprises about 4 g creatine anhydrous and about 5 g creatinine nitrate. In some aspects, the composition comprises about 4 g creatine and between about 4 g and about 5 g creatinine. In some aspects, the amount of creatine in the solid composition is provided as a composition consisting of 1.5 g creatine nitrate and 3.5 g creatine monohydrate. In such composition, the amount of creatinine is 5 g anhydrous creatinine. In another embodiment, the composition comprises 5 g creatine nitrate is 5 g and 4 g anhydrous creatinine. In another implementation, the composition comprises 3 g creatine nitrate, 2 g anhydrous creatine, and 5 g creatinine.

The corresponding liquid composition (for example, liquid food product or liquid dietary supplement formulation) would further comprise water or some other water-based composition or liquid, such as a commercial sports drink formulation, to dissolve the creatine compound and the creatinine compound. In some aspects, the amount of water or some other water-based composition or liquid is about 500 ml, about 475 ml, about 16 fluid oz, or about 240 ml. In some embodiments, the liquid composition further comprises a pH buffer, wherein the pH buffer adjusts the pH of the liquid composition to 4.4 or less, for example, between about 4.2 and about 4.4. In certain embodiments, the pH of the liquid composition is about 4.4.

The concentration of creatine from the creatine compound in the liquid composition of the disclosure does not fall below 70%, preferably 90% or 95%, of the original concentration of creatine during storage, for example, at or around room temperature for at least a month, three months, six months, or a year. In some embodiments, the concentration of creatine in the liquid composition of the disclosure remains steady. In particular, the concentration of creatine after 30 days of storage at room temperature remains the same or higher than the concentration of creatine on day 1. In some aspects, the concentration of creatine after 30 days is higher than the concentration of creatine after 1 day.

Compositions and/or formulations of the present invention may be in any form for administration, whether solid or liquid. For example, the composition and/or formulation is in the form of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, or combinations thereof for example. It is convenient to have an efficacious dose of creatine in a good-tasting, already mixed drink. Thus, liquid compositions where the creatine is stable at a greater than 95% amount over a long time (for example, 30 days, a month, three months, six months, or a year) without requiring refrigeration are preferred.

Compositions and/or formulations of the present invention may also include at least one additional ingredient.

In one aspect, the additional ingredient produces a composition with intermediate rigidity and/or intermediate fluidity properties between solid and liquid, which is described interchangeably herein as a semisolid composition, a semiliquid composition, or a quasi-solid composition. In such embodiments, the additional ingredient includes but is not limited to a semi-solid lipophilic vehicle, a paste, a solubilizer, thickener, or a gelling agent. In some aspects, the additional ingredient in a solid composition produces a semiliquid composition. In other aspects, the additional ingredient in a liquid composition produces a semisolid composition.

In some aspects, the at least one additional ingredient comprises an acceptable additive for human consumption. Accordingly, the at least one additional ingredient is at least one additive selected from the group consisting of: a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, and a thickener. These additives may be solids or liquids, and the type of additive may be generally chosen based on the type of administration being used. Those of ordinary skill in the art will be able to readily select suitable additives from the disclosure in this document. In particular implementations, the acceptable additive is a pharmaceutically acceptable. For example, pharmaceutically acceptable additives include, calcium phosphate, cellulose, stearic acid, croscarmellose cellulose, magnesium stearate, and silicon dioxide. In another aspect, the at least one additional ingredient comprises an acceptable carrier for human consumption. Accordingly, the at least one additional ingredient is at least one carrier selected from the group consisting of: an excipient, a lubricant, a binder, a disintegrator, a diluent, an extender, a solvent, a suspending agent, a dissolution aid, an isotonization agent, a buffering agent, a soothing agent, and an amphipathic lipid delivery system. In some aspects, the at least one additional ingredient is selected from the group consisting of: a flavoring agent, a colorant, a viscosity modifier, a preservative, a fragrance, an amino acid, a salt of an amino acid, a vitamin, a mineral, a fatty acid, an enzyme, a co-enzyme, a mono-glyceride, a di-glyceride, a tri-glyceride ester oils emulsifiers, a hydrolyzed protein, whey protein, a stabilizer, a flow modifier, a chelating agent, an antioxidant, an anti-microbial, a benzoate, an alcohol, an ester of para-hydroxybenzoic acid, a propionate, and a surfactant.

In particular embodiment, the compositions and/or formulations of the present invention further comprise at least one source of nitrate ($NO_3^-$). In some aspects, a source of nitrate is an inorganic nitrate salt (for example, sodium nitrate or potassium nitrate). In other aspects, a source of nitrate is a nitrate salt of an amino acid or a nitrate salt of an amino acid derivative, for example, the nitrate salt of arginine, agmatine, beta alanine, betaine, carnitine, creatine, citrulline, glutamine, L-histidine, isoleucine, leucine, norvaline, ornithine, valine, aspartic acid, cysteine, glycine, lysine, methionine, phenylalanine, proline, taurine, or tyrosine. Where the creatine compound of the composition is creatine nitrate, the at least one source of nitrate in the composition does not include creatine nitrate. In still other aspects, a source of nitrate is a botanical source, for example juice, extract, powder, or other derivative product from cabbage, spinach, beet leaf, beetroot, artichoke, asparagus, broad bean, eggplant, garlic, onion, green bean, mushroom, pea, pepper, potato, summer squash, sweet potato, tomato, watermelon, broccoli, carrot, cauliflower, cucumber, pumpkin, chicory, dill, turnip, savoy cabbage, celeriac, Chinese cabbage, endive, fennel, kohlrabi, leek, parsley, celery, cress, chervil, lettuce, rocket (rucola), and other vegetables or fruits known to containing high levels of nitrate. In preferred embodiments, the botanical source of nitrate is beet juice.

In certain embodiments, the at least one source of nitrate ($NO_3^-$) provides between about 50 mg and about 2000 mg nitrate ($NO_3^-$), for example, between about 60 mg and 1200 mg nitrate ($NO_3^-$).

Creatine Compound

The creatine compound includes anhydrous creatine or a salt, solvate, or hydrate of creatine. While the creatine compound may be any salt of creatine, it is preferable the creatine compound is creatine nitrate. Other creatine compounds for use in the disclosed compositions include single administration physiologically active salts, creatine's tautomeric, polymeric and/or isomeric forms, creatine's analog forms, or creatine's derivative forms. It should be noted that as disclosed herein, the creatine compound does not include creatine esters and peptides, such as creatine ethyl ester and creatinyl-L-leucine. Creatine esters and peptides are unsuitable for the compositions described herein although they are generally stable in an acidic environment. Creatine esters and peptides are not actual sources of creatine, because cleavage of the peptide bond results in the formation of creatinine instead of creatine. Also in many cases creatine esters and peptides may be excreted unchanged to at least some degree.

As a non-limiting example, the creatine compound may be selected from the group consisting of: creatine nitrate, creatine anhydrous, creatine monohydrate, creatine hydrochloride, creatine acetate, creatine malate, creatine ascorbate, creatine phosphate, creatine adipate, creatine aspartate, creatine caproate, creatine cinammate, creatine formate, creatine formic acid solvate, creatine fumarate, creatine gluconate, creatine glucuronate, creatine glycerophosphate, creatine glycolate, creatine lactate, creatine hydrobromide, creatine malonate, creatine methanesulfonate, creatine oleate, creatine orotate, creatine nicotinate, creatine pyroglutamate, creatine pyruvate, creatine stearate, creatine tartrate, creatine succinate, creatine citrate, creatine ferulate, and creatine toluenesulfonate.

Creatine nitrate has been synthesized and patented by the applicants. The applicants found that creatine nitrate is more stable in aqueous compositions than creatine monohydrate and buffered creatine (kre-alkalyn). In preferred embodiments, the creatine compound is creatine nitrate.

The chemical stability of creatine nitrate (CN), creatine monohydrate (CM), and buffered creatine (BC) were examined under two different storage conditions: (1) 37° C. in pH 2.5 buffer and (2) 40° C. in pH 6.8 buffer. A concentration of about 10 mg/ml of CN, CM and BC were prepared in both pH 2.5 and pH 6.8 buffer and stored in stability chambers in screw capped bottles at 37° C. and 40° C., respectively. The degradation rate constants for CN, CM and BC at 37° C. in pH 2.5 buffer were 0.075±0.001, 0.119±0.011, and 0.108±0.002 per day, respectively, while the degradation rate constants at 40° C. in pH 6.8 buffer were 0.115±0.001, 0.015±0.001, and 0.013±0.002 per day, respectively. The pH of CN samples at 40° C. in pH 6.8 buffer changed from 2.83±0.01 to 4.31±0.01 within a period of 12 days. The pH changes noticed at 37° C. in pH 2.5 buffer samples over the same period of time for CM, and BC were 3.08±0.01 to 4.12±0.01 and 3.11±0.01 to 4.16±0.01, respectively. No significant change in pH was observed for the rest of the samples. No change in the color and the clarity was noticed over 12 days.

All the creatine samples followed first order degradation kinetics under both these experimental conditions. The degradation rate constants for CN was found to be higher at 40° C. in pH 6.8 buffer as compared to at 37° C. in pH 2.5 buffer. However, both CM and BC showed a faster rate of degradation at 37° C. in pH 2.5 buffer than at 40° C. in pH 6.8 buffer. The major degradation product detected was creatinine. For CN the increase in pH was higher at 40° C. in pH 6.8 buffer as compared to 37° C. in pH 2.5 buffer. However, opposite effect was noticed for both CM and BC.

When creatine nitrate is combined with creatinine before dissolving into a solution, the concentration of creatine in the solution remains constant even after storage at around 25° C. for a long period of time, for example, at least a month (see Examples 1 and 2).

Creatinine Compound

The creatinine compound of the compositions of the disclosure is selected from any form of creatinine, including single administration physiologically active salts, solvates, or hydrates, creatinine's tautomeric, polymeric and/or isomeric forms, creatinine's analog forms, or creatinine's derivative forms. The creatinine compound includes anhydrous creatinine or a salt or hydrate of creatinine. The specific kind of creatinine compound used in the composition of the invention affects the stability of creatine. The salts of creatinine for use in the composition include salts of creatinine formed using either an organic acid or an inorganic acid, although the stability of creatine nitrate could be affected with every different creatinine salt chosen. Such salts include, but are not limited to: creatinine nitrate, creatinine hydrochloride, creatinine acetate, creatinine malate, creatinine ascorbate, creatinine phosphate, creatinine adipate, creatinine aspartate, creatinine caproate, creatinine cinammate, creatinine formate, creatinine fumarate, creatinine gluconate, creatinine glucuronate, creatinine glycerophosphate, creatinine glycolate, creatinine lactate, creatinine hydrobromide, creatinine malonate, creatinine methanesulfonate, creatinine oleate, creatinine orotate, creatinine nicotinate, creatinine pyroglutamate, creatinine pyruvate, creatinine ferulate, creatinine citrate, creatinine stearate, creatinine tartrate, creatinine succinate, and creatinine toluenesulfonate, creatinine pyruvate.

EXAMPLES

The disclosure is further illustrated by the following examples that should not be construed as limiting. The contents of all references, patents, and published patent applications cited throughout this application are incorporated herein by reference in their entirety for all purposes.

1. Stability of Creatine in a Liquid Composition Comprising Creatine Nitrate and Creatinine Over a Period of 14 Months: Storage at Room Temperature (25° C.)

Figure 1:
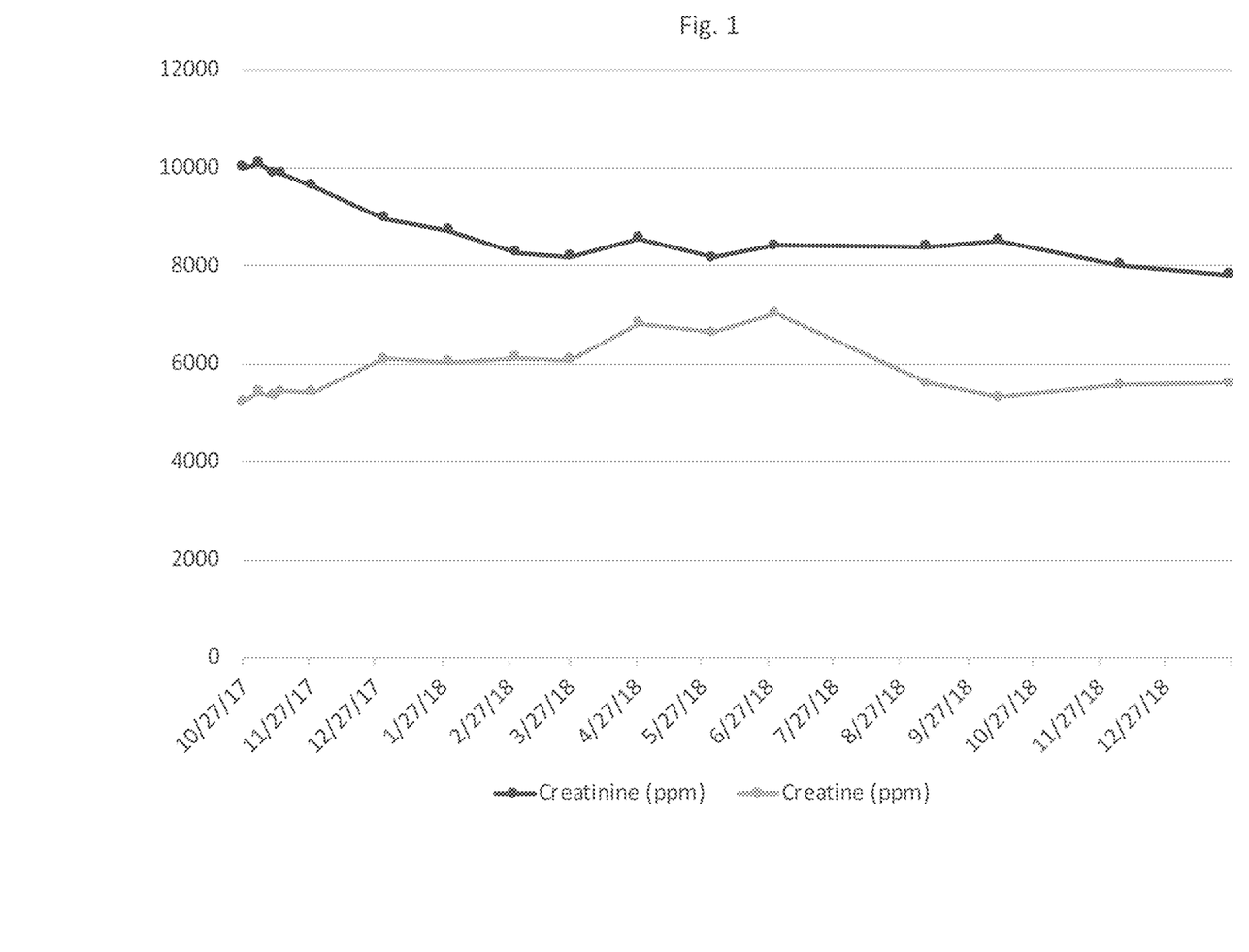
FIG. 1 is a graph tracking the change in the creatine and creatinine content of an exemplary liquid composition of the disclosure stored at room temperature (about 25° C.) over a period of 14 months.

Creatine nitrate (5 g, equaling 25.5 mmol or 3.34 g creatine) was combined with creatinine (4 g equaling 35.4 mmol creatinine) and then dissolved in 500 ml of water. The solution was left at room temperature (about 25° C.). Over the period of 14 months, the amount of creatine and creatinine in ppm were measured (see Table 1 and FIG. 1).

TABLE 1

| Analysis Date | Creatinine (ppm) | Creatine (ppm) |
| --- | --- | --- |
| 2017 Oct. 27 | 10014.99 | 5244.27 |
| 2017 Nov. 3 | 10086.3 | 5417.66 |
| 2017 Nov. 10 | 9909.82 | 5342.83 |
| 2017 Nov. 14 | 9880.29 | 5443.84 |
| 2017 Nov. 28 | 9644.02 | 5422.60 |
| 2017 Dec. 31 | 8969.06 | 6108.93 |
| 2018 Jan. 30 | 8723.39 | 6041.02 |
| 2018 Mar. 2 | 8282.80 | 6127.22 |
| 2018 Mar. 27 | 8183.38 | 6075.87 |
| 2018 Apr. 28 | 8557.34 | 6830.62 |
| 2018 Jun. 1 | 8161.07 | 6647.78 |
| 2018 Jun. 30 | 8422.65 | 7029.07 |
| 2018 Sep. 8 | 8401.57 | 5611.32 |
| 2018 Oct. 11 | 8522.94 | 5319.45 |
| 2018 Dec. 6 | 8015.59 | 5559.72 |
| 2019 Jan. 26 | 7812.69 | 5602.11 |

Contrary to the observations in the prior art regarding the various forms of creatine converting to creatinine over time, the creatine content in the liquid creatine nitrate-creatinine composition has not reduced over time in the liquid formulation of the invention, thereby creating a unique stable creatine solution that may be used in foods, dietary supplements, and pharmaceutical preparations for example. The amount of creatine at day 30 of the current invention is at a minimum the same concentration, if not a higher concentration of creatine than the amount of creatine at day 1. In fact, in the surprising results of the original experiment, the creatine content in the liquid formulation of the invention actually increased from the initial creatine concentration, as the solution comprising creatine nitrate as the creatine compound and creatinine is stored for longer than a month at room temperature.

2. Stability of Creatine in a Liquid Composition Comprising Creatine Nitrate and Creatinine Over a Period of 12 Months: Storage at Room Temperature (25° C.)

Figure 2:
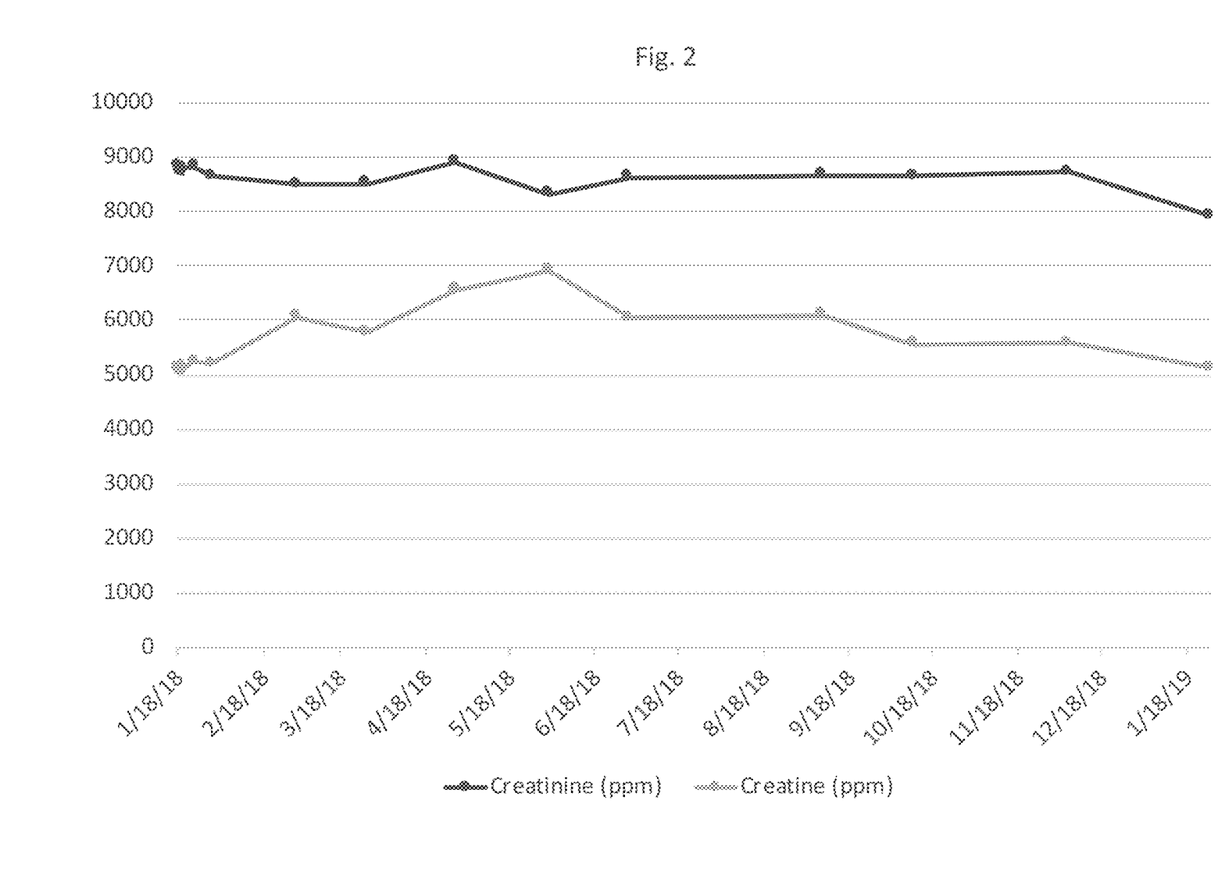
FIG. 2 is a graph tracking the change in the creatine and creatinine content of an exemplary liquid composition of the disclosure stored at room temperature (about 25° C.) over a period of a year.

Creatine nitrate (5 g, equaling 25.5 mmol creatine or 3.34 g creatine) was combined with creatinine (4 g equaling 35.4 mmol creatinine) and then dissolved in 500 ml of water. The solution was left at room temperature (about 25° C.). Surprisingly, the creatine content in the liquid increased from the initial creatine concentration as the liquid was stored at room temperature for longer than a month (see Table 2 and FIG. 2).

TABLE 2

| Analysis Date | Creatinine (ppm) | Creatine (ppm) |
|---|---|---|
| 2018 Jan. 18 | 8837.51 | 5130.22 |
| 2018 Jan. 19 | 8710.34 | 5057.29 |
| 2018 Jan. 20 | 8804.51 | 5147.82 |
| 2018 Jan. 24 | 8818.74 | 5231.74 |
| 2018 Jan. 30 | 8638.97 | 5198.99 |
| 2018 Mar. 2 | 8493.77 | 6065.45 |
| 2018 Mar. 27 | 8521.45 | 5768.23 |
| 2018 Apr. 28 | 8906.06 | 6562.30 |
| 2018 Jun. 1 | 8326.96 | 6914.92 |
| 2018 Jun. 30 | 8633.51 | 6039.40 |
| 2018 Sep. 8 | 8666.33 | 6106.06 |
| 2018 Oct. 11 | 8640.62 | 5564.04 |
| 2018 Dec. 6 | 8724.83 | 5579.68 |
| 2019 Jan. 26 | 7926.65 | 5121.64 |

3. Stability of Creatine in a Liquid Composition Comprising Creatine Nitrate and Creatinine Over a Period of 7 Months: Storage at Room Temperature (25° C.)

Figure 3:
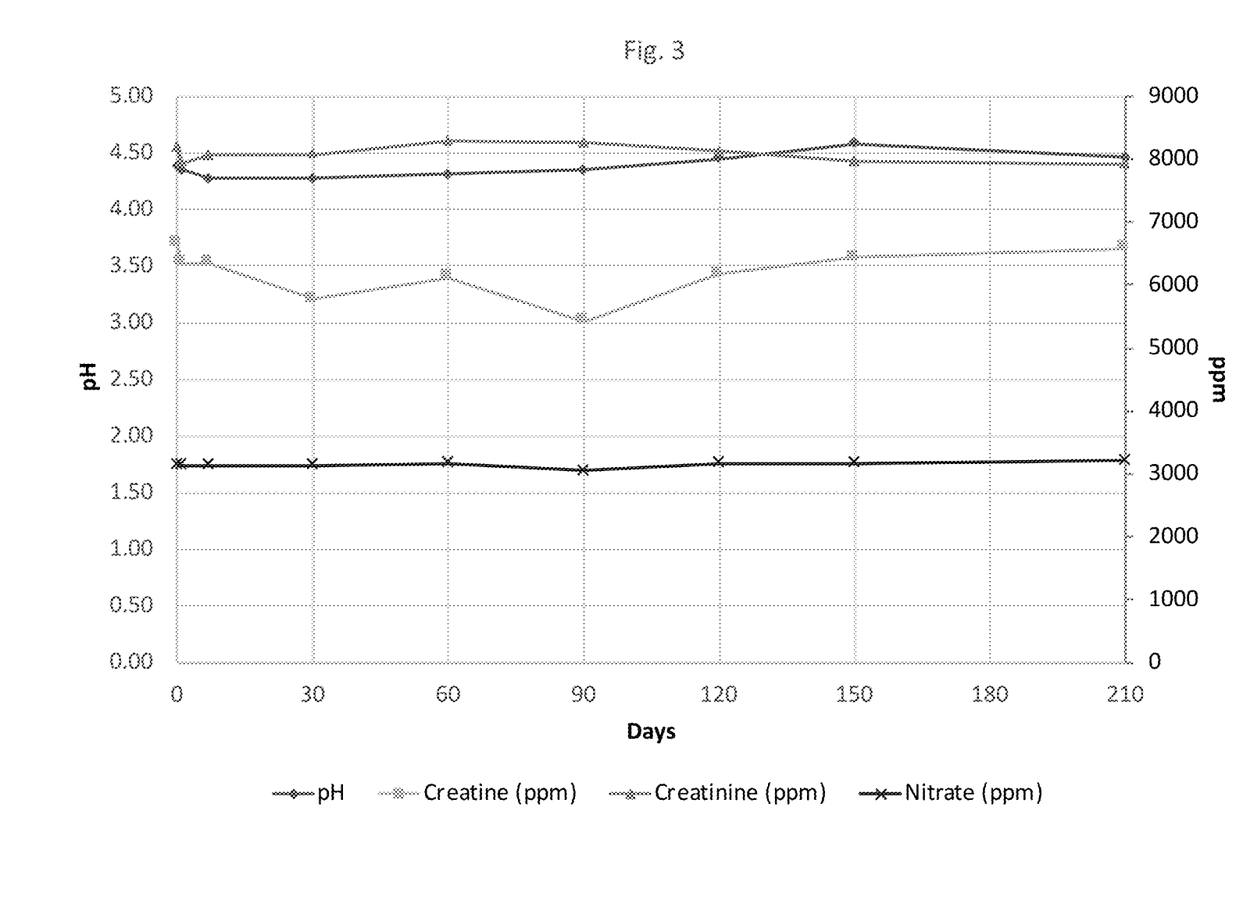
FIG. 3 is a graph tracking the change in pH and in the creatine, creatinine, and nitrate content of a liquid composition produced from dissolving 5 g creatine nitrate and 4 g creatinine with 500 ml water. The liquid composition was stored at room temperature (about 25° C.).

In 500 ml of water at room temperature, 5 g creatine nitrate and 4 g creatinine were added and creatine, creatinine, nitrate and pH levels were assessed at the time point intervals indicated in the table below. Creatine content did not degrade, but actually increased, after 210 days of storage (see Table 3 and FIG. 3).

TABLE 3

| Analysis Day | Creatine (ppm) | Creatinine (ppm) | Nitrate (ppm) | pH |
|---|---|---|---|---|
| 0 | 6673 | 8182 | 3153 | 4.39 |
| 1 | 6356 | 7951 | 3134 | 4.35 |
| 7 | 6357 | 8066 | 3142 | 4.28 |
| 30 | 5770 | 8080 | 3142 | 4.28 |
| 60 | 6119 | 8293 | 3177 | 4.31 |
| 90 | 5420 | 8260 | 3060 | 4.35 |
| 120 | 6180 | 8130 | 3170 | 4.45 |
| 150 | 6430 | 7970 | 3180 | 4.58 |
| 210 | 6590 | 7920 | 3220 | 4.46 |

4. Stability of Creatine in a Liquid Composition Comprising Creatine Nitrate and Creatinine Over a Period of 7 Months: Storage in Refrigeration (2-8° C.)

Figure 4:
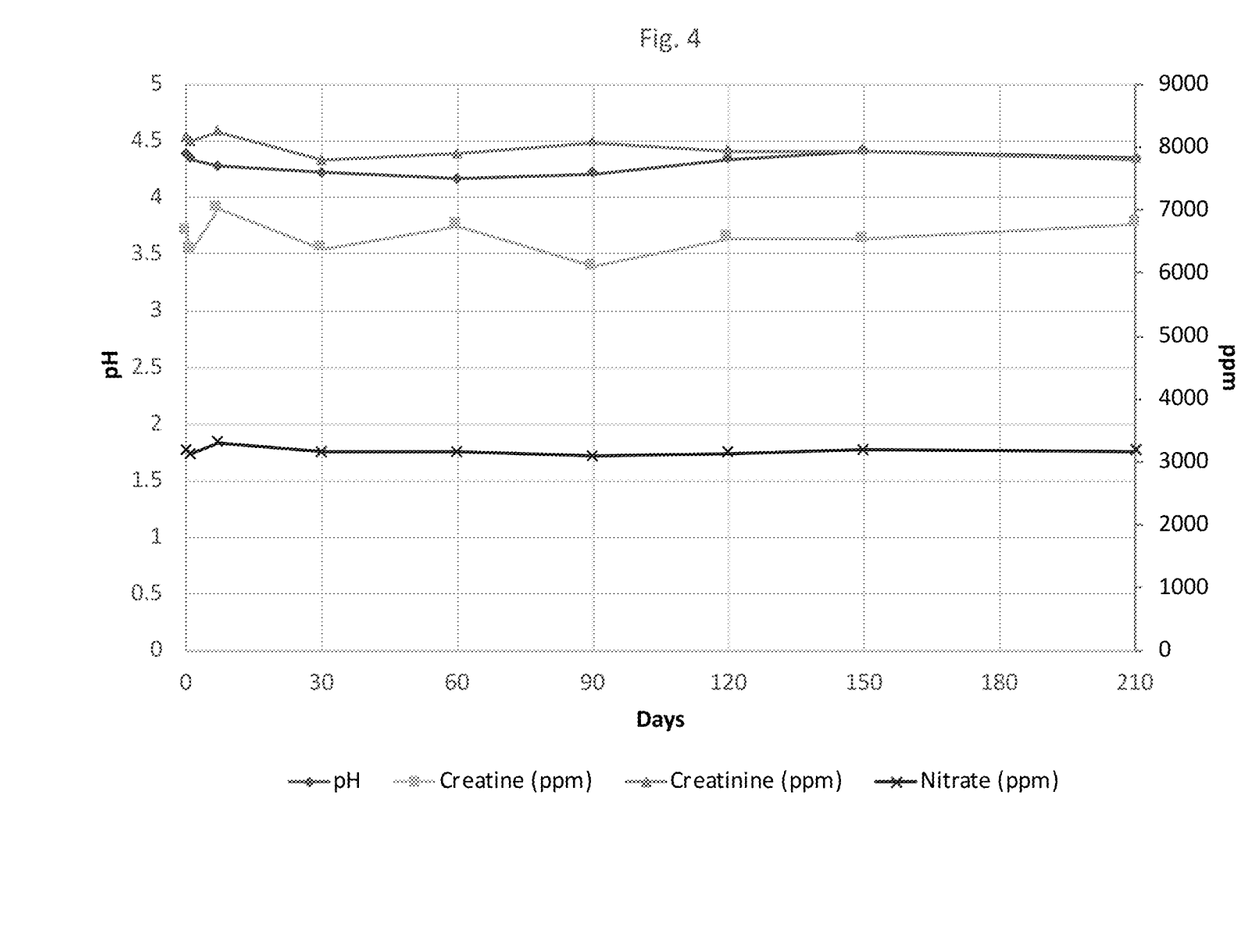
FIG. 4 is a graph tracking the change in pH and in the creatine, creatinine, and nitrate content of a liquid composition produced from dissolving 5 g creatine nitrate and 4 g creatinine with 500 ml water. The liquid composition was stored in refrigeration (2-8° C.).

In 500 ml of water at a temperature of between 2-8° C., 5 g creatine nitrate and 4 g creatinine were added. The solution was stored in refrigeration (2-8° C.). Creatine, creatinine, nitrate and pH levels were assessed at the time point intervals indicated in Table 4 and FIG. 4.

TABLE 4

| Analysis Day | Creatine (ppm) | Creatinine (ppm) | Nitrate (ppm) | pH |
|---|---|---|---|---|
| 0 | 6647 | 8151 | 3189 | 4.39 |
| 1 | 6358 | 8097 | 3128 | 4.34 |
| 7 | 7024 | 8241 | 3304 | 4.28 |
| 30 | 6389 | 7799 | 3156 | 4.22 |
| 60 | 6748 | 7903 | 3157 | 4.17 |
| 90 | 6110 | 8070 | 3100 | 4.21 |
| 120 | 6560 | 7940 | 3140 | 4.34 |
| 150 | 6530 | 7940 | 3190 | 4.41 |
| 210 | 6780 | 7810 | 3180 | 4.35 |

Similar to the previous example, creatine levels remained stable during the whole 210 days regardless of refrigeration. This is very important. Previous approaches to the problem of creatine degradation tried to use refrigeration to slow-down creatine degradation, but it was surprisingly discovered that refrigeration, which carries a lot of drawbacks like need of a refrigerator, or other cooling device, increased costs, hurdles in transportation, etc., is not required to ensuring the stability of creatine a liquid composition in the invention disclosed herein.

5. Stability of Creatine in a Liquid Composition Comprising Creatine Nitrate and Creatinine Over a Period of 7 Months: Storage in Refrigeration (2-8° C.)

Figure 5:
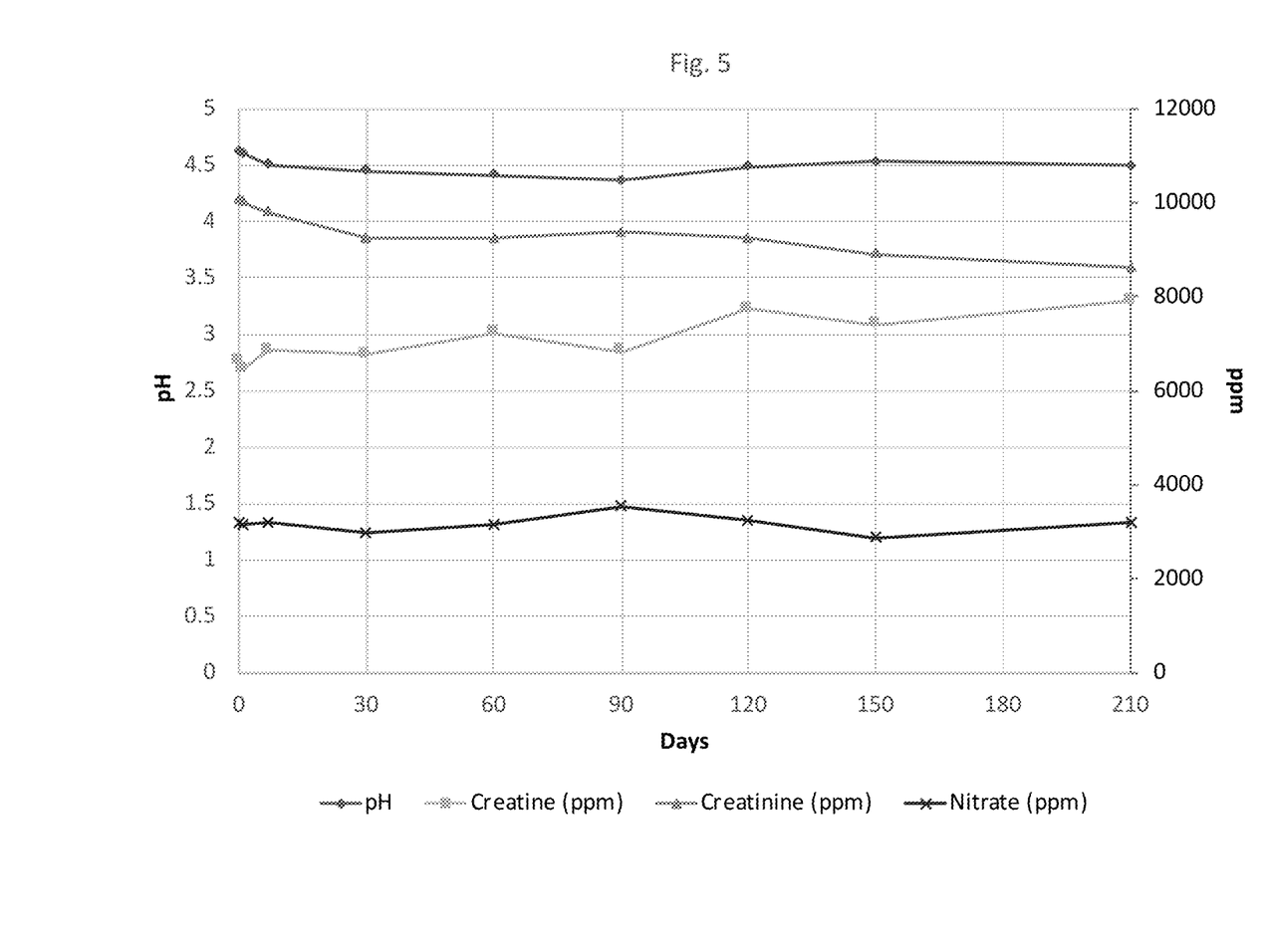
FIG. 5 is a graph tracking the change in pH and in the creatine, creatinine, and nitrate content of a liquid composition produced from dissolving 5 g creatine nitrate and 5 g creatinine with 500 ml water. The liquid composition was stored at room temperature (about 25° C.).

In 500 ml of water at room temperature, 5 g creatine nitrate and 5 g creatinine were added and creatine, creatinine, nitrate and pH levels were assessed at the time point intervals indicated in Table 5 and FIG. 5.

TABLE 5

| Analysis Day | Creatine (ppm) | Creatinine (ppm) | Nitrate (ppm) | PH |
|---|---|---|---|---|
| 0 | 6630 | 10075 | 3179 | 4.63 |
| 1 | 6468 | 10010 | 3148 | 4.61 |
| 7 | 6852 | 9791 | 3194 | 4.51 |
| 30 | 6774 | 9251 | 2984 | 4.45 |
| 60 | 7240 | 9242 | 3148 | 4.41 |
| 90 | 6840 | 9370 | 3540 | 4.37 |
| 120 | 7740 | 9250 | 3240 | 4.49 |
| 150 | 7420 | 8910 | 2870 | 4.53 |
| 210 | 7920 | 8630 | 3200 | 4.50 |

As can be seen in the table and in FIG. 5, creatine levels actually increased while creatinine levels decreased. This is unprecedented: in an acidic environment of 4.4, which is well known to favor the degradation of creatine to creatinine, the opposite occurred. Not only was creatine not degraded, the total creatine content in the composition increased. The increased creatine content may be due to the conversion of creatinine to creatine.

6. Stability of Creatine Added to a Commercial Energy Drink

Figure 6:
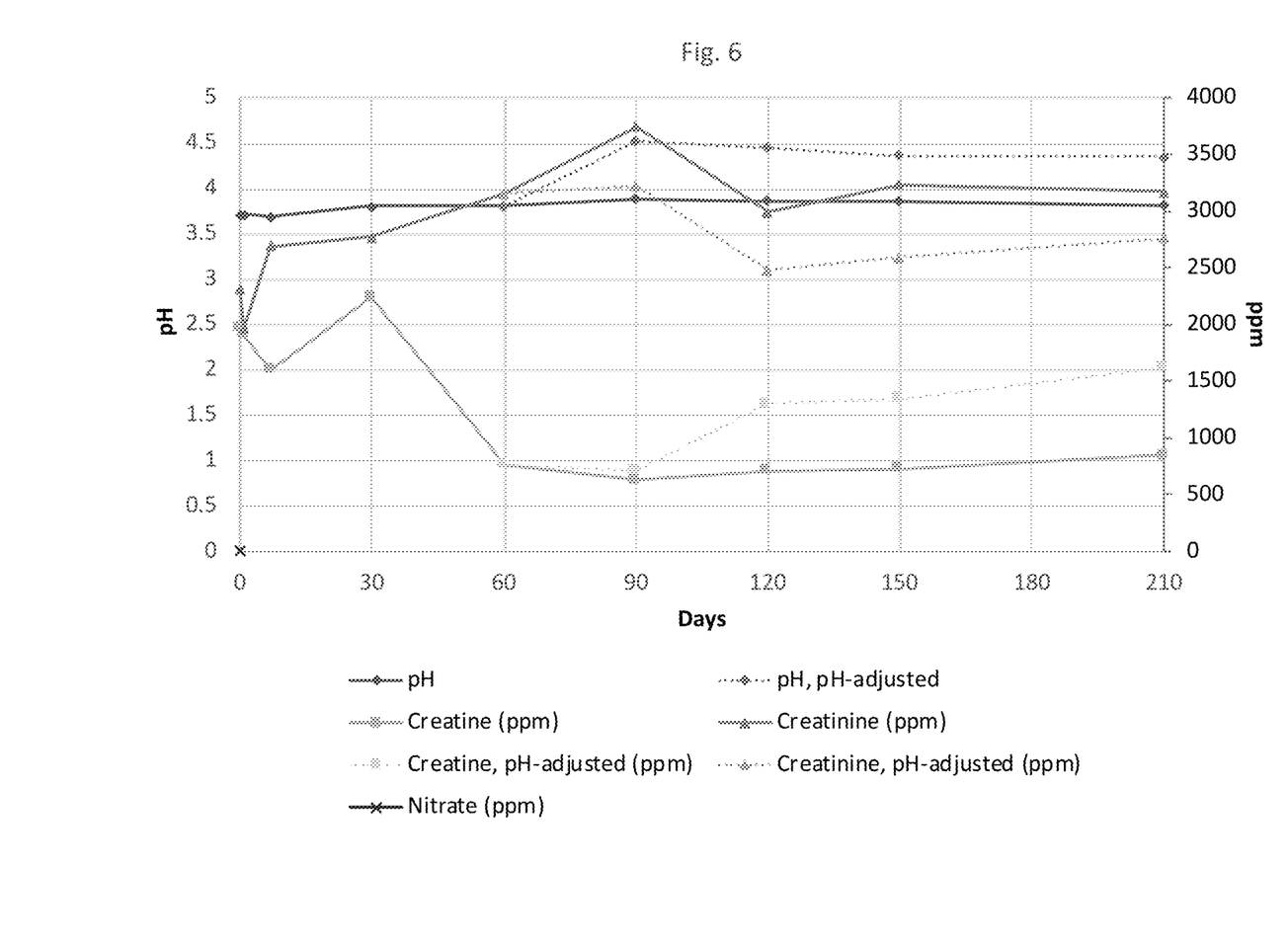
FIG. 6 is graph tracking the change in pH and in the creatine, creatinine, and nitrate content of a liquid composition produced from dissolving 1.5 g creatine nitrate and 1 g creatinine with 500 ml of a multicomponent energy drink. The liquid composition was stored at room temperature (about 25° C.). At day 60, the pH of the half of the solution was adjusted to 4.4 to study the effect of slightly less acidic pH on the levels of creatine and creatinine in the solution.

Creatine nitrate and creatinine were dissolved in a multicomponent energy drink (1.5 g creatine nitrate and 1 g creatinine added to 500 ml of the energy drink), and the changes in pH and creatine and creatinine content were measured (See Table 6 and FIG. 6). After the addition of creatine nitrate and creatinine, the drink had a resulting pH of 3.71. Creatine continued to degrade through day 60, where 62% of the beginning creatine content was seemingly lost. On day 60, the liquid was split in half to examine the influence of the pH in the stability of the creatine-creatinine composition. In one half, the pH was adjusted to 4.4 using a pH buffer. Increasing the pH resulted in increased creatine content despite the pH remaining at an acidic level. At day 210, 82% of the original creatine content was restored in the half of the solution with adjusted pH. Thus, maintaining the pH to about 4.4 is important for creatine's stability even in the presence of creatinine.

TABLE 6

| Analysis Day | Creatine (ppm) | Creatinine (ppm) | Nitrate (ppm) | PH |
|---|---|---|---|---|
| Day 0 | 1972 | 2306 | 951 | 3.71 |
| Day 1 | 1911 | 1965 | 878 | 3.71 |
| Day 7 | 1597 | 2689 | 996 | 3.69 |
| Day 30 | 2240 | 2770 | 891 | 3.8 |
| Day 60 | 769 | 3150 | 946 | 3.8 |
| Day 90 | 632 | 3740 | 984 | 3.88 |
| Day 90, pH adjusted | 713 | 3220 | | 4.52 |

TABLE 6-continued

| Analysis Day | Creatine (ppm) | Creatinine (ppm) | Nitrate (ppm) | PH |
|---|---|---|---|---|
| Day 120 | 708 | 2990 | 950 | 3.86 |
| Day 120, pH adjusted | 1300 | 2480 | | 4.45 |
| Day 150 | 726 | 3230 | 915 | 3.86 |
| Day 150, pH adjusted | 1350 | 2590 | | 4.36 |
| Day 210 | 845 | 3170 | 944 | 3.82 |
| Day 210, pH adjusted | 1620 | 2760 | | 4.35 |

7. Human Study Comparing the Effects of Administering Creatine Monohydrate, Creatine Nitrate, and the Disclosed Composition A human study was designed to evaluate the effects of combining creatine and creatinine for bioavailability and performance. Ten healthy human volunteers (aged 20-25 years) were used to evaluate and compare the effects of administering 3 g creatine monohydrate (CrM), 3 g creatine nitrate (CN, providing about 2 g creatine) or a composition comprising 3 g creatine nitrate and 3 g creatinine (CN-CRN).

Each human subject was administered CN, CrM, or CN-CRN with a glass of water with a washout period of 7 days among each experiment. Creatine serum levels were assessed at 0, 5, 30, 45, 60, 90, 120 minutes after administration of CN, CrM, or CN-CRN. The average peak serum creatine concentrations at 60-min sampling interval were significantly higher in CN-CRN group (183.7±15.5 µmol/L), as compared to CN group (163.8±12.9 µmol/L) and CrM group (118.6±12.9 µmol/L) ($P<0.001$). CN-CRN resulted in a more powerful rise in serum creatine levels comparing to either CN or CrM after single-dose intervention, as evaluated with the area under the concentration-time curve calculation (701.1±62.1 (µmol/L)×min vs. 622.7±62.9 (µmol/L)×min vs. 466.3±47.9 (µmol/L)×min; $P<0.001$). It is of great note that the much higher levels of serum creatine in the CN-CRN were achieved with 33% less creatine than the creatine monohydrate group. Accordingly, co-administration of creatine and creatinine significantly improves serum creatine concentration in human subjects.

Based on muscle biopsies taken from the subject, higher creatine muscle levels were seen when the subjects were treated with CN-CRN.

Nine of the subjects did not report any negative side effects as measured by a side effect reporting questionnaire. However, one subject reported gastrointestinal disturbances with all three treatments (CrM, CN, and CN-CRN).

Liver and kidney function as measured by ALT AST remained unchanged while GFR estimation showed a slight less than 10% clinically insignificant reduction.

8. Creatinine Neutralizes Caffeine's Counteraction on the Ergogenic Actions of Creatine Vandenberghe et al. found that the ergogenic effect of creatine on muscle was completely eliminated by caffeine intake (Vandenberghe et al., 1996). As Hespel et al.'s experiments showed, this might be due to opposite effect of caffeine and creatine on muscle relaxation time. However, Applicants discovered that co-administration of creatine with creatinine eliminated the neutralizing effect of caffeine with respect of creatine's ergogenic actions on muscle.

A 35-year-old male subject (weight of 240 lb) ingested creatine with creatinine supplement formulation for six days. During the period of supplementation, the subject was advised to abstain from creatine rich foods and caffeine sources. Specifically, the subject ingested a dose of 5 g creatine nitrate and 5 g creatinine four times a day (total daily supplementation of 20 g creatine nitrate and 20 g creatinine) for five days. On the fifth and sixth day, the subject also consumed 350 mg caffeine in the morning alongside the morning dose of creatine and creatinine.

Prior to supplementation the maximum weight the subject could push for three knee extensions was 365 lb. On the morning of the sixth day of supplementation, the subject could push 380 lb for three knee extensions. Thus, an increase in strength and endurance was observed despite the co-administration of caffeine with creatine.

9. Creatinine Increases the Solubility of Creatine in Water

A common problem with creatine in the production of liquid supplements is creatine's low solubility in water. Creatine has a solubility of 13.3 g/l in water, or 13.3 mg/ml, in 25° C. While one option of increasing the solubility of creatine in water is to reduce the pH of the solution, the cost of this approach is the reduced stability of creatine in solution. Applicants surprisingly found that creatinine, an alkaline substance, can increase creatine solubility of creatine even while it causes the pH of the solution to increase. Thus, in a solution of 10 g creatinine in one liter of water, the maximum solubility of creatine at 25° C. in water increased to 15.8 mg/ml or 15.8 g/L, which is an 18% increase of creatine's solubility in water. The increased water solubility of creatine in the presence of creatinine without the need to reduce the pH of the solution enables the manufacture of solutions with higher concentration of creatine for use as an injectable or intravenous solution, where the preferred pH range is between 7-8 (Lee et al., 2013).

REFERENCES CITED (WHICH ARE ALL INCORPORATED BY REFERENCE HEREIN IN THEIR ENTIRETIES)

Alraddadi et al., Pharmaceutics., 2018, 10(1). pii: E31.
Barsotti et al., Kidney Int, 1975 (7) Suppl: S299-S301.
Cannon et al., Am J Physiol., 1990, 259(6 Pt 2):R1214-9.
Dash et al., J Pharm Sci., 2002, 91(3):708-718.
Dash and Sawhney, J Pharm Biomed Anal., 200229(5):939-45.
Deldicque et al., Eur J Appl Physiol., 2008, 102(2):133-43.
Edgar and Shiver, J Am Chem Soc., 1925 47:1179-1188.
Gangopadhyay et al., World Academy of Science, Engineering and Technology International Journal of Physical and Mathematical Sciences, 2019, 13(2): 195.
Ganguly et al., AAPS PharmSciTech, 2003, 4:119.
Giovannetti et al., Clin. Sci., 1969, 36:445-452.
Lee et al., International Journal of Pharmaceutics, 2003, 253: 111-119.
Lis and Bijan, Physiol. Chem. & Physics. 1970, 2:293-299.
McCall and Persky, Subcell Biochem. 2007, 46:261-73.
Tambaru et al., AIP Conference Proceedings 1823, 020095 (2017).
Vandenberghe et al., J Appl Physiol (1985), 1996, 80(2): 452-7.

We claim:

1. A method of improving the oral bioavailability of creatine, the method comprising co-administering to a human subject an effective amount of creatine, creatinine, and nitrate ($NO_3^-$), wherein the effective amount of creatine is at least about 500 mg, the effective amount of creatinine is at least about 500 mg, and the effective amount of nitrate ($NO_3^-$) is at least about 50 mg nitrate ($NO_3^-$).

2. The method of claim 1, wherein the effective amount of nitrate ($NO_3^-$) is between about 50 mg and about 1200 mg nitrate ($NO_3^-$).

3. The method of claim 1, wherein the effective amount of nitrate ($NO_3^-$) is between about 50 mg and about 1500 mg nitrate ($NO_3^-$).

4. The method of claim 1, wherein the effective amount of nitrate ($NO_3^-$) is between about 60 mg and about 1500 mg nitrate ($NO_3^-$).

5. The method of claim 1, wherein the effective amount of nitrate ($NO_3^-$) is between about 60 mg and about 1200 mg nitrate ($NO_3^-$).

6. The method of claim 1, wherein the effective amount of creatine is at least about 1000 mg, the effective amount of creatinine is at least about 1000 mg, and the effective amount of nitrate ($NO_3^-$) is at least about 100 mg.

7. The method of claim 1, wherein the effective amount of creatine is at least about 2 g, the effective amount of creatinine is at least about 2 g, and the effective amount of nitrate ($NO_3^-$) is at least about 500 mg.

8. The method of claim 1, wherein the effective amount of creatine is at least about 5 g, the effective amount of creatinine is at least about 3 g, and the effective amount of nitrate ($NO_3^-$) is at least about 1000 mg.

9. A method of improving the oral bioavailability of creatine, the method comprising co-administering to a human subject an effective amount of creatine, creatinine, and nitrate ($NO_3^-$), wherein the molar ratio of the amount of nitrate ($NO_3^-$) to the amount of creatinine is between about 20:1 and about 1:9.

10. The method of claim 9, wherein the molar ratio of the amount of nitrate ($NO_3^-$) to the amount of creatinine is between about 10:1 and about 1:1.

11. The method of claim 9, wherein the molar ratio of the amount of nitrate ($NO_3^-$) to the amount of creatinine is between about 3:1 and about 1:3.

12. The method of claim 9, wherein the molar ratio of the amount of nitrate ($NO_3^-$) to the amount of creatinine is between about 2:1 and about 1:4.

13. The method of claim 9, wherein the molar ratio of the amount of creatine to the amount of nitrate ($NO_3^-$) is between about 20:1 and about 1:9.

14. The method of claim 9, wherein the molar ratio of the amount of creatine to the amount of nitrate ($NO_3^-$) is between about 10:1 and about 1:1.

15. The method of claim 9, wherein the molar ratio of the amount of creatine to the amount of nitrate ($NO_3^-$) is between about 3:1 and about 1:3.

16. The method of claim 9, wherein the molar ratio of the amount of creatine to the amount of nitrate ($NO_3^-$) is between about 2:1 and about 1:4.

17. The method of claim 1, wherein the oral bioavailability of the effective amount of creatine administered is greater than the oral bioavailability of creatine when administered alone.

18. A method of improving the oral bioavailability of creatine, the method comprising administering to a human subject a composition comprising an effective amount of creatine and creatinine, wherein the molar ratio of the effective amount of creatine and creatinine is 1:1 to 1:1.7 and the pH of the composition is 4.2 to 4.4.

19. The method of claim 18, wherein the method further comprises administering an effective amount of nitrate ($NO_3^-$), wherein the effective amount of nitrate ($NO_3^-$) and the effective amount of creatine are administered as creatine nitrate.

* * * * *